United States Patent [19]

Tanaka et al.

[11] Patent Number: 5,137,811

[45] Date of Patent: Aug. 11, 1992

[54] METHOD FOR DIAGNOSING PERIODONTAL DISEASES WITH A SUBSTRATE SPECIFIC FOR AMINOPEPTIDASE ACTIVITY OF PERIODONTOPATHIC BACTERIA

[75] Inventors: Toshiyuki Tanaka, Takarazuka; Hirohisa Suido, Kawachinagano; Masakazu Nakamura, Takatsuki, all of Japan

[73] Assignee: Sunstar Kabushiki Kaisha, Osaka, Japan

[21] Appl. No.: 459,185

[22] Filed: Dec. 29, 1989

Related U.S. Application Data

[63] Continuation-in-part of Ser. No. 76,875, Jul. 23, 1987.

[30] Foreign Application Priority Data

Jul. 29, 1986 [JP] Japan .................. 61-179716
Sep. 30, 1986 [JP] Japan .................. 62-233848
May 9, 1987 [JP] Japan .................. 62-113122

[51] Int. Cl.$^5$ .......... C12Q 1/37; C12Q 1/30; C12Q 1/04; A61K 37/02
[52] U.S. Cl. .......... 435/24; 435/27; 435/23; 435/34; 550/300; 550/330; 550/331; 550/802
[58] Field of Search .......... 435/24, 27, 34, 23; 530/300, 330, 331, 802

[56] References Cited

U.S. PATENT DOCUMENTS

4,457,866  7/1984  Karges et al. .................. 435/4

FOREIGN PATENT DOCUMENTS

0018112  10/1980  European Pat. Off.
82/100641  3/1982  World Int. Prop. O.

OTHER PUBLICATIONS

Hyyppa et al., *Studies on immunologic and inflamm . . .*, vol. 8, pp. 500–507, 1981.

Nakamura et al., *Dipeptidyl arylamidase activity of . . .*, vol. 25, pp. 157–160, 1984.

Todo et al., *Histochemical observations on . . .*, vol. 11, pp. 921–930, 1966.

Abiko et al., *Glycylprolyl dipeptidylaminopeptidase . . .*, J. Dent. Res., vol. 64, No. 2, pp. 106–111, 1985.

Nakamura et al., *Salivary Enzymes: Origin and . . .*, J. of Periodontal Res., vol 18, pp. 559–569, 1983.

Zambon et al., *Effect of periodontal therapy on . . .*, J. of Periodontal Res., vol. 20, pp. 652–659, 1985.

Saido et al., *Arylamidase Activities of oral bacteria . . .*, J. Dent. Res., vol. 65, No. 11, 1335–1340, Nov. 1986.

Nakamura et al., *Amino peptidase activity of . . .*, J. of Periodontal Research, vol. 17, pp. 597–603, 1982.

*Primary Examiner*—David M. Naff
*Assistant Examiner*—Mike Meller
*Attorney, Agent, or Firm*—Wegner, Cantor, Mueller & Player

[57] ABSTRACT

A method for diagnosing contraction or progress of periodontal diseases is carried and by determining periodontopathic bacteria specific aminopeptidase activity in a specimen by using as a substrate for the enzyme. The substrate is either or both compounds of the formula:

$$X—Z—Arg—Y \qquad [1]$$

wherein Arg is arginine residue; X is or an amino blocking group; Y is a color developing group attached to the C-terminal of Arg; and Z is an amino acid or peptide residue composed of 1 or 2 amino acids or their blocked derivatives, the C-terminal of which is attached to the N-terminal of Arg, and $$X'—Z'—Pro—Y' \qquad [2]$$

wherein Pro is proline residue; X' is an amino blocking group; Y' is a color developing group attached to the C-terminal of Pro; and Z' is an amino acid or peptide residue composed of 0 to 4 amino acids or their blocked derivatives, the C-terminal of which is attached to the N-terminal of Pro.

8 Claims, No Drawings

METHOD FOR DIAGNOSING PERIODONTAL DISEASES WITH A SUBSTRATE SPECIFIC FOR AMINOPEPTIDASE ACTIVITY OF PERIODONTOPATHIC BACTERIA

This is a continuation-in-part application of U.S. patent application Ser. No. 076,875 filed Jul. 23, 1987.

FIELD OF THE INVENTION

The present invention relates to a method for diagnosing periodontal diseases. More particularly, it relates to a method which can detect certain pathogenic oral microorganisms for periodontal diseases specifically, readily and promptly to diagnose contraction or progress of such diseases.

BACKGROUND OF THE INVENTION

Recently, bacteriological researches on periodontal diseases have advanced and, as the results, it has been found that many spirochetes are detected in sites with periodontal diseases and have good correlation with various clinical indices. Further, it has been also found that anaerobic gram negative bacteria are main pathogenic oral microorganisms for periodontal diseases. Among them, Black-pigmented *Bacteroides* such as *B. gingivalis* are particularly noted and many reports about their phathogenicities are present.

Then, attempts are made to detect these pathogenic bacteria in the oral cavity and to apply the results to clinical use so that periodontal diseases can be prevented or treated by diagnosing contraction or progress thereof.

However, there are some drawbacks in detection of these pathogenic oral bacteria by a bacteriological method. For example, detection requires highly skilled technique and special equipments such as use of a dark field microscope and handling of anaerobes, and involves complicated operations. Further, it takes long time and requires skill for cultivation and analysis of the result. Therefore, there are still many difficulties in application thereof to clinical practice.

From the immunological point of view, some attempts are made to detect the presence of the pathogenic microorganisms by determining antibody titer in blood which is humoral immunity to the pathogenic microorganisms, or determining lymphocyte blastformation which is cellular immunity. However, preparation of a specimen requires complicated operations and practical application is still difficult.

Under these circumstances, the present inventors have studied intensively to make detection of the pathogenic oral microorganisms for periodontal diseases applicable to clinical practice possible. As the result, the present inventors have found that some spirochetes in the oral cavity have periodontopathic bacteria specific aminopeptidase activities and Black-pigmented *Bacteroides* such as *B. gingivalis, B. intermedius, B. corporis, B. melaninoqenicus, B. denticola* and the like also have similar activities, which can be detected specifically, readily and promptly using particular substrates with precisely reflecting periodontal disease conditions.

It has been known heretofore in the prior art that oral spirochetes and *B. gingivalis* produce a trypsin-like enzyme and fibrinolysin [see, Journal of Clinical Microbiology, 97-102 (January, 1982); Microbios Letters, 25, 157-160 (1984); Journal of Dental Research, 65, 11, 1335-1340 (November, 1986) and Journal of Periodontal Research, 21, 95-100 (1986)]. However, it is difficult to use these enzymes as indices because of problems in correlation with clinical conditions and specificity in detection.

OBJECTS OF THE INVENTION

The main object of the present invention is to provide a clinically applicable method for diagnosing periodontal diseases which can detect certain pathogenic oral microorganisms for periodontal diseases specifically, readily and promptly to diagnose contraction or progress of such diseases.

This object as well as other objects and advantages of the present invention will become apparent to those skilled in the art from the following description.

SUMMARY OF THE INVENTION

According to the present invention, there is provided a method for diagnosing contraction or progress of periodontal diseases which comprises determining periodontopathic bacteria specific aminopeptidase activity in a specimen by using as a substrate for the enzyme either or both compounds of the formula:

$$X\text{-}Z\text{-}Arg\text{-}Y \qquad [1]$$

wherein Arg is arginine residue; X is an amino blocking group; Y is a color developing group attached to the C-terminal of Arg; and Z is an amino acid or peptide residue composed of 1 or 2 amino acids or their blocked derivatives, the C-terminal of which is attached to the N-terminal of Arg, and

$$X'\text{-}Z'\text{-}Pro\text{-}Y' \qquad [2]$$

wherein Pro is proline residue; X' is an amino blocking group; Y' is a color developing group attached to the C-terminal of Pro; and Z' is an amino acid or peptide residue composed of 0 to 4 amino acids or their blocked derivatives, the C-terminal of which is attached to the N-terminal of Pro.

That is, in one aspect of the present invention, the method comprises determining the enzymatic activity by using as the substrate a compound of the formula [1].

In another aspect of the present invention, the method comprises determining the enzymatic activity by using as the substrate a compound of the formula [2].

In still another aspect of the present invention, the method comprises determining the enzymatic activity by using as the substrate both compounds of the formulas [1] and [2].

According to the present invention, the diagnosis of contraction or progress of periodontal diseases can be readily and promptly carried out by reacting a specimen such as saliva, dental plaque, gingival crevicular fluid or the like with the substrate of the formulas [1] and/or [2], preferably, under neutral conditions (pH 6.0 to 8.5) and determining the intensity of enzymatic hydrolysis activity by color development with a coloring reagent.

Thereby, according to the present invention, a desired diagnosis of contraction or progress of periodontal diseases can be made readily and promptly without requiring any special equipment or high technique, and adequate treatment and prevention of periodontal disease can be conducted.

DETAILED DESCRIPTION OF THE INVENTION

The compounds of the formulas [1] and [2] used as the substrate in the present invention is known or, at least, readily prepared by known peptide synthesis.

In the formulas [1] and [2], the amino blocking groups represented by X and X' may be any amino blocking group known in peptide synthesis such as formyl, acetyl, succinyl, t-butoxycarbonyl, benzoyl, carbobenzoxy, p-toluenesulfonyl and the like.

The color developing group Y is a member selected from the class consisting of $\beta$-naphthylamine, 4-methoxy-2-naphthylamine, p-nitrophenol, 7-amino-4-methoxycoumarin, dimethyl-5-aminoisophthalate and 7-amino-4-trifluoromethylcoumarin groups.

The color developing group Y' may be any one used in determination of enzymatic activity by color development (including determination of absorption in ultraviolet, visible and infrared regions as well as determination of fluorescence). The typical examples include groups derived from $\beta$-naphthylamine, 4-methoxy-2-naphthylamine, p-nitroaniline, p-nitrophenol, 7-amino-4-methoxycoumarin, dimethyl-5-aminoisophthalate, 7-amino-4-trifluoromethylcoumarin and the like. Particularly preferred groups are those derived from $\beta$-naphthylamine, 4-methoxy-2-naphthylamine, p-nitroaniline and p-nitrophenol which can show visually detectable color development with a suitable coloring reagent.

Z group may be any amino acid or peptide residue which composed of 1 to 4 amino acids or their blocked derivatives wherein C-terminal is attached to N-terminal of the arginine residue. Preferably, the C-terminal amino acid in the group Z is glycine, lysine, arginine, phenylalanine or their blocked derivatives. The blocked derivative includes a OH blocked serine, SH blocked cysteine, $\beta$- or $\gamma$-COOH blocked aspartic acid or glutamic acid, thereof is blocked by a suitable blocking group such as benzyl.

Z' group may be any amino acid or peptide residue which composed of 0 to 4 amino acids or their blocked derivatives (i.e., when the number of the amino acids is 0, the group Z' is not present in the formula [2]) wherein C-terminal is attached to N-terminal of the proline residue. Preferably, the C-terminal amino acid in the group Z' is glycine, lysine, phenylalanine or their blocked derivatives. The blocked derivative includes a OH blocked serine, SH blocked cysteine, $\beta$- or $\gamma$-COOH blocked aspartic acid or glutamic acid, thereof is blocked by a suitable blocking groups such as benzyl.

When the compound of the formula [1] is used together with the compound of the formula [2], X and X', Y and Y' as well as Z and Z' may be the same or different, respectively. However, preferably, Y and Y' are the same because color can be developed by using the same coloring reagent, simultaneously.

The configuration of each amino acid residue in the compounds of the formulas [1] and [2] is not specifically limited so long as it can be served as a substrate of a periodontopathic bacteria specific aminopeptidase.

The substrate used in the method of the present invention may be in any preparation form so long as the compounds of the formulas [1] and [2] can react as the substrate for the aminopeptidase from the specimen. Basically, it may be an aqueous solution of the compounds of the formulas [1] and/or [2], preferably, containing a buffer so that the pH thereof is adjusted to 6.0 to 8.5, when the measurement is carried out. There can be used any buffer which is usually used, for example, Tris-HCl buffer, phosphate buffer, borate buffer, veronal buffer, HEPES buffer or the like. The aqueous solution can be prepared according to a conventional method, for example, by dissolving the compounds of the formulas [1] and/or [2] and, if any, a buffer in distilled water. Further, optionally, other additives such as preservatives, antibiotics and the like may be added.

In the present invention, preferably, the substrate can be used in a final concentration of 10 nM to 10 mM. When both compounds of the formulas [1] and [2] are used, the weight ratio of [1]/[2] is preferably 1:10 to 10:1. Preferably, the buffer can be used in a final concentration of 1 mM to 1M. The above-mentioned aqueous solution can be so prepared that it contains either or both compounds of the formulas [1] and [2] and, if any, a buffer in these concentrations, and can be directly used for a test. Alternatively, it can be prepared into a concentrated solution which can be optionally diluted with distilled water to give a solution containing the substrate in a desired concentration before use.

The preparations used in the present invention includes solid preparations, for example, dry powder or granules obtained from the above-mentioned aqueous solution according to a known method; powder mixture obtained by mixing powder ingredients; granules obtained from such a powder mixture; or liquid preparations soaked in carriers such as filter paper, paper disc, sponge, polymers and the like.

The substrate can be used in the form of a kit which comprises a reagent containing either or both compounds of the formulas [1] and [2] in combination with other reagents such as a buffer, a coloring reagent and the like.

The coloring reagent can be appropriately selected according to the groups Y and Y' in the compounds of the formulas [1] and [2]. For example, when the group is derived from $\beta$-naphthylamine, 4-methoxy-2-naphthylamine, p-nitroaniline or p-nitrophenol, there can be used a solution of Fast Garnet GBC or Fast Blue BB or a salt thereof such as a diazonium salt or a salt with zinc chloride in water, ethanol, an acetate buffer, 2-methoxyethanol or a mixture thereof in an concentration of 0.01 to 5% by weight, or a 0.5 to 5M aqueous solution of sodium hydroxide, potassium hydroxide or acetic acid. These solutions or concentrated solutions thereof and further their solidified preparations can be used in combination with the reagent containing either or both compounds of the formulas [1] and [2] as the kit.

For carrying out the method for diagnosing contraction or progress of periodontal diseases of the present invention, firstly, a specimen is collected. The specimen can be collected according to a known process. For example, gingival crevicular fluid and saliva can be collected with filter paper, capillary, paper point and the like, and dental plaque can be collected with a swab, curette, scaler and the like.

Then, the substrate, whose final concentration is adjusted to 10 nM to 10 mM, is contacted with the specimen, for example, in a test tube, microtiter plate, vial, plastic cuvette or the like to subject the mixture to hydrolysis reaction, preferably, at pH of 6.0 to 8.5. This reaction is usually conducted at 15° to 45° C., preferably, 25° to 45° C. The reaction time varies depending on a particular specimen and reaction temperature. Preferably, the reaction is carried out at 37° C. for 15 minutes to 72 hours.

After completion of the reaction, a coloring reagent is added and then the presence of color development or its intensity is evaluated with the naked eye, or with a spectrophotometer or a fluorophotometer to determine the presence or intensity of periodontopathic bacteria specific aminopeptidase activity in the specimen. Thus, contraction or progress of periodontal diseases can be diagnosed.

The following Experiments and Examples further illustrate the present invention in detail but are not to be construed to limit the scope thereof.

EXPERIMENT 1

Periodontopathic bacteria specific aminopeptidase activity of various kinds of oral anaerobes Oral anaerobes, i.e., four strains of *Treponema denticola*, five strains of *B. gingivalis*, four strains of *Actinobacillus actinomycetemcomitans*, four strains of *Capnocytophaga sp.* and three strains of *Fusobacterium nucleatum* were tested for hydrolytic activity to the substrate of aminopeptidase enzyme as follows.

The strains of *Treponema* were anaerobically cultivated using TYGVS media at 37° C. for 7 days, while other bacterial strains were cultivated using brain heart infusion broth at 37° C. for 48 to 72 hours. Each culture was diluted to obtain a bacterial cell suspension, the absorption at 660 nm of which was 1.0.

Substrate compounds for aminopeptidase enzyme having various color developing groups derived from β-naphthylamine were dissolved in 0.1M Tris-HCl buffer (pH 7.0) at the concentration of 0.2 mM to obtain substrate solutions.

To the substrate solution (1.5 ml) was added the above cell suspension (0.3 ml) and reacted at 37° C. for 60 minutes. After completion of the reaction, a coloring reagent [prepared by dissolving diazonium salt of Garnet GBC in 1M acetate buffer (containing 10% Tween 20, pH: 4.2) at the concentration of 0.5 mg/ml] was added and, after 15 minutes, the absorption at 525 nm was determined with a spectrophotometer.

On the basis of the average amount of released β-naphthylamine in each strain, the hydrolytic activity was expressed as follows:

−: release amount <5 nmol/ml
±: 5 ≦release amount <10 nmol/ml
+: 10 ≦release amount <20 nmol/ml
++: 20 ≦release amount <40 nmol/ml
+++: release amount ≧40 nmol/ml The results are shown in Table 1. Abbreviations used in Table 1 mean the following substrate compounds.

A: alanine-β-naphthylamide
G: glycine-β-naphthylamide
R: arginine-β-naphthylamide
K: lysine-β-naphthylamide
GR: glycyl-arginine-β-naphthylamide
RR: arginyl-arginine-β-naphthylamide
RG: arginyl-glycine-β-naphthylamide
KR: lysyl-arginine-β-naphthylamide
FR: phenylalanyl-arginine-β-naphthylamide
GK: glycyl-lysine-β-naphthylamide
GF: glycyl-phenylalanine-β-naphthylamide
PFR: prolyl-phenylalanyl-arginine-β-naphthylamide
BzGR: N-benzoyl-glycyl-arginine-β-naphthylamide
CxRR: N-carbobenzoxy-arginyl-arginine-β-naphthylamide
CxFR: N-carbobenzoxy-phenylalanyl-arginine-β-naphthylamide
CxKR: N-carbobenzoxy-lysyl-arginine-β-naphthylamide
CxVGR: N-carbobenzoxy-valyl-glycyl-arginine-β-naphthylamide
BzVGR: N-benzoyl-valyl-glycyl-arginine-β-naphthylamide

TABLE 1

| Strain | A | G | R | K | GR | RR | RG | KR | FR | GK | GF | PFR | BzGR |
|---|---|---|---|---|---|---|---|---|---|---|---|---|---|
| *Treponema denticola* | − | − | − | − | + | +++ | − | + | + | − | − | +++ | ++ |
| *Bacteroides gingivalis* | − | − | − | − | ++ | + | ++ | ++ | + | + | ++ | +++ | +++ |
| *Actinobacillus actinomycetemcomitans* | − | − | − | − | − | − | − | − | − | − | − | − | − |
| *Capnocytophaga sp.* | +++ | + | +++ | +++ | ± | + | + | + | ± | + | ± | − | − |
| *Fusobacterium nucleatum* | − | − | − | − | − | − | − | − | − | − | − | − | − |

| Strain | CxRR | CxFR | CxKR | CxVGR | BzVGR |
|---|---|---|---|---|---|
| *Treponema denticola* | ++ | +++ | ++ | +++ | +++ |
| *Bacteroides gingivalis* | +++ | +++ | ++ | +++ | +++ |
| *Actinobacillus actinomycetemcomitans* | − | − | − | − | − |
| *Capnocytophaga sp.* | − | − | − | − | − |
| *Fusobacterium nucleatum* | − | − | − | − | − |

As is shown in Table 1, among the oral anaerobes, pathogenic spirochete for periodontal diseases (*Treponema denticola*) and *B. gingivalis* show periodontopathic bacteria specific aminopeptidase activity, and specifically hydrolyze the compound of the formula [1] among various substrate compounds.

EXPERIMENT 2

According to the same manner as described in Experiment 1, periodontopathic bacteria specific aminopeptidase activity was tested by using four strains of *Treponema denticola*, five strains of *B. gingivalis*, three strains of *B. intermedius*, two strains of *B. melaninogenicus*, two strains of *Actinomyces israelli*, four strains of *Actinobacillus actinomycetemcomitans* and three strains of *Fusobacterium nucleatum*. The results are shown in Table 2. Abbreviations used in Table 2 mean the following substrate compounds.

A: alanine-β-naphthylamide
G: glycine-β-naphthylamide
R: arginine-β-naphthylamide
K: lysine-β-naphthylamide
P: proline-β-naphthylamide
VA: valyl-alanine-β-naphthylamide
LG: leucyl-glycine-β-naphthylamide
SY: seryl-tyrosine-β-naphthylamide
FP: phenylalanyl-proline-β-naphthylamide
KP: lysyl-proline-β-naphthylamide
GP: glycyl-proline-β-naphthylamide
CxKP: N-carbobenzoxy-lysyl-proline-β-naphthylamide BzGP: N-benzoyl-glycyl-proline-β-naphthylamide
BzGFP: N-benzoyl-glycyl-phenylalanyl-proline-β-naphthylamide
CxVKP: N-carbobenzoxy-valyl-lysyl-proline-β-naphthylamide
CxPAGP: N-carbobenzoxy-prolyl-alanyl-glycyl-proline-β-naphthylamide
BzRGFP: N-benzoyl-arginyl-glycyl-phenylalanyl-proline-β-naphthylamide
ScGPLGP: N-succinyl-glycyl-prolyl-leucyl-glycyl-proline-β-naphthylamide amount < 80 nmol/ml" and "+ + + +" means "release amount ≧ 80 nmol/ml".

TABLE 3

| Strain | Substrate | | | | | | | |
|---|---|---|---|---|---|---|---|---|
| | GR | BzGR | CxVGR | GP | CxKP | BzRGFP | GR + GP | BzGR + CxKP |
| Treponema denticola | + | + + | + + + | + + | + | + + | + + + | + + + |
| B. gingivalis | + + | + + + | + + + | + + + | + + | + + | + + + | + + + + |
| Actinobacillus actinomycetemcomitans | − | − | − | − | − | − | − | − |
| Actinomyces israelli | − | − | − | − | − | − | − | − |
| Fusobacterium nucleatum | − | − | − | − | − | − | − | − |

| Strain | Substrate | |
|---|---|---|
| | CxVGR + BzRGFP | BzGP + BzRGFP |
| Treponema denticola | + + + + | + + + |
| B. gingivalis | + + + + | + + + + |
| Actinobacillus actinomycetemcomitans | − | − |
| Actinomyces israelli | − | − |
| Fusobacterium nucleatum | − | − |

As shown in Table 3, when the compound of the formula [1] is used together with the compound of the formula [2], the enzymatic activity is increased twice or three times as much as that obtained by using either compound of the formula [1] or [2] alone.

EXPERIMENT 4

Correlation for clinical state (1)

Specimens of gingival crevicular fluid were collected

TABLE 2

| Strain | Substrate | | | | | | | | | | | | | |
|---|---|---|---|---|---|---|---|---|---|---|---|---|---|---|
| | A | G | R | K | P | VA | LG | SY | FP | KP | GP | CxKP | BzGP | BzGFP |
| Treponema denticola | − | − | − | − | + | − | − | − | + + | + + | + + | + | + + | + + + |
| B. gingivalis | − | − | − | − | − | + + | + | + + | + + | + + + | + + + | + + | + + | + + |
| B. intermedius | − | − | − | − | − | − | − | + | + + | + | + + | + + + | + + + |
| B. corporis | − | − | − | − | − | ± | + + | ± | + | + + | + + | + + | + + | + + |
| B. melaninogenicus | − | − | − | − | − | ± | + + + | ± | + | + + | + + | + + | + + | + + |
| B. denticola | − | − | − | − | − | ± | + + | ± | + | + + | − | + + | + + | + + |
| Fusobacterium nucleatum | − | − | − | − | − | − | − | − | − | − | − | − | − | − |
| Actinobacillus actinomycetemcomitans | − | − | − | − | − | − | − | − | − | − | − | − | − | − |
| Actinomyces israelli | − | − | − | − | − | − | − | − | − | − | − | − | − | − |

| Strain | Substrate | | | |
|---|---|---|---|---|
| | CxVKP | CxPAGP | BzRGFP | ScGPLGP |
| Treponema denticola | + + | + + + | + + | + |
| B. gingivalis | + + | + | + + | ± |
| B. intermedius | + + | + + + | + + + | + |
| B. corporis | + + | + + | + + | ± |
| B. melaninogenicus | + + | + + + | + + + | ± |
| B. denticola | + + | + + + | + + + | ± |
| Fusobacterium nucleatum | − | − | − | − |
| Actinobacillus actinomycetemcomitans | − | − | − | − |
| Actinomyces israelli | − | − | − | − |

Likewise, the results of Table 2 shows that, among the oral anaerobes, pathogenic spirochete for periodontal diseases (*Treponema denticola*) and Black-pigmented Bacteroides show periodontopathic bacteria specific aminopeptidase activity, and specifically hydrolyze the compound of the formula [2] among various substrate compounds.

EXPERIMENT 3

According to the same manner as described in Experiment 1, periodontopathic bacteria specific aminopeptidase activity was tested by using four strains of *Treponema denticola*, five strains of *B. gingivalis*, four strains of *Actinobacillus actinomycetemcomitans*, two strains of *Actinomyces israelli* and three strains of *Fusobacterium nucleatum*. The results are shown in Table 3. Abbreviations in Table 3 are the same as those in Tables 1 and 2. Hydrolytic activity "+ + +" means "40≦release with paper points from five subjects who were considered to be healthy from their clinical state, six subjects with gingivitis and six subjects with periodontitis. Each specimen was dispersed in Ringer's solution (1.5 ml), and the relative amount of spirochete to total bacteria:

$$\frac{\text{Number of spirochetes/Ringer's solution (ml)}}{\text{Number of all bacteria/Ringer's solution (ml)}} \times 100 \ (\%)$$

was determined with a phase contrast microscope. Further, the Ringer's solution (0.3 ml) was tested for hydrolytic activity using the substrate solution prepared in the same manner as described in Experiment 1. As substrates, there were used compounds of the formula [1], i.e., N-benzoylvalyl-glycyl-arginine-β-naphthylamide (BzVGR) and N-carbobenzoxy-valyl-glycyl-arginine-β-naphthylamide (CxVGR) were used.

The results are shown in Table 4. In table 4, hydrolytic activity was visually evaluated and expressed as follows:
- −: orange
- +: dark orange
- ++: brown
- +++: dark brown

TABLE 4

| Subject | Amount of Spirochete (%) | Substrate BzVGR | Substrate CxVGR |
|---|---|---|---|
| Healthy | | | |
| 1 | 0.1 | − | − |
| 2 | 2.5 | + | + |
| 3 | 1.1 | − | − |
| 4 | 0.6 | − | − |
| 5 | 1.3 | − | − |
| Gingivitis | | | |
| 1 | 7.3 | + | + |
| 2 | 16.7 | + | + |
| 3 | 20.5 | ++ | ++ |
| 4 | 6.8 | − | − |
| 5 | 7.3 | − | − |
| 6 | 14.4 | + | + |
| Periodontitis | | | |
| 1 | 45.2 | +++ | +++ |
| 2 | 30.3 | +++ | +++ |
| 3 | 34.6 | +++ | +++ |
| 4 | 21.2 | +++ | +++ |
| 5 | 40.3 | +++ | +++ |
| 6 | 35.1 | +++ | +++ |

As shown in Table 4, hydrolytic activity has correlation for the amount of spirochete and the clinical state. There is no difference in reactivity between the two substrates.

EXPERIMENT 5

According to the same manner as described in Experiment 4, hydrolytic activity was tested by using the compounds of the formula [2], i.e., lysyl-proline-$\beta$-naphthylamide (KP) and N-carbobenzoxy-prolyl-alanyl-glycylproline-$\beta$-naphthylamide (CxPAGP) as the substrates. The results are shown in Table 5.

TABLE 5

| Subject | Amount of Spirochete (%) | Substrate KP | Substrate CxPAGP |
|---|---|---|---|
| Healthy | | | |
| 1 | 0.1 | − | − |
| 2 | 2.5 | + | + |
| 3 | 1.1 | − | − |
| 4 | 0.6 | − | − |
| 5 | 1.3 | − | − |
| Gingivitis | | | |
| 1 | 7.3 | + | + |
| 2 | 16.7 | + | + |
| 3 | 20.5 | ++ | ++ |
| 4 | 6.8 | − | − |
| 5 | 7.3 | − | − |
| 6 | 14.4 | + | + |
| Periodontitis | | | |
| 1 | 45.2 | +++ | +++ |
| 2 | 30.3 | +++ | +++ |
| 3 | 34.6 | +++ | +++ |
| 4 | 21.2 | +++ | +++ |
| 5 | 40.3 | +++ | +++ |
| 6 | 35.1 | +++ | +++ |

Likewise, hydrolytic activity has correlation for the clinical state and there is no difference in reactivity between both substrates.

EXPERIMENT 6

According to the same manner as described in Experiment 4, hydrolytic activity was tested by using the compounds of the formulas [1] and [2], i.e., glycyl-proline-$\beta$naphthylamide (GP), N-benzoyl-arginyl-glycyl-phenylalanylproline-$\beta$-naphthylamide (BzRGFP), N-carbobenzoxy-valylglycyl-arginine-$\beta$-naphthylamide (CxVGR) and N-benzoylglycyl-arginine-$\beta$-naphthylamide (BzGR) alone or in combination. Hydrolytic activity was determined by measuring absorption at 525 nm ($OD_{525}$) and expressed as follows.
- −: $OD_{525} < 0.1$
- +: $0.1 \leq OD_{525} < 0.2$
- ++: $0.2 \leq OD_{525} < 0.4$
- +++: $0.4 \leq OD_{525} < 0.8$
- ++++: $0.8 \leq OD_{525}$ The results are shown in Table 6.

TABLE 6

| Subject | Amount of Spirochete (%) | CxVGR | BzGR | GP | BzRGFP | CxVGR + GP | BzGR + BzRGFP |
|---|---|---|---|---|---|---|---|
| Healthy | | | | | | | |
| 1 | 0.1 | − | − | − | − | − | − |
| 2 | 2.5 | + | ± | ± | + | + | + |
| 3 | 1.1 | − | − | − | − | − | − |
| 4 | 0.6 | − | − | − | − | − | − |
| 5 | 1.3 | − | − | − | − | − | − |
| Gingivitis | | | | | | | |
| 1 | 7.3 | + | + | + | + | + | + |
| 2 | 16.7 | + | + | + | + | ++ | ++ |
| 3 | 20.5 | ++ | ++ | ++ | ++ | ++ | ++ |
| 4 | 6.8 | − | − | − | − | − | − |
| 5 | 7.3 | − | − | − | − | − | − |
| 6 | 14.4 | + | ± | + | + | + | ++ |
| Periodontitis | | | | | | | |
| 1 | 45.2 | +++ | ++ | +++ | +++ | ++++ | ++++ |
| 2 | 30.3 | +++ | ++ | +++ | +++ | ++++ | ++++ |
| 3 | 34.6 | +++ | ++ | +++ | +++ | ++++ | ++++ |
| 4 | 21.2 | +++ | ++ | ++ | +++ | ++++ | ++++ |
| 5 | 40.3 | +++ | ++ | +++ | +++ | ++++ | ++++ |
| 6 | 35.1 | +++ | ++ | +++ | +++ | ++++ | ++++ |

As shown in Table 6, when the compound of the formula [1] is used together with the compound of the formula [2], hydrolytic activity of the specimen is considerably increased.

EXPERIMENT 7

Correlation with clinical state (2)

A saliva mixture was collected from a group consisting of ten healthy subjects and centrifuged to obtain a supernatant. Likewise, centrifuged supernatants were obtained from a group of ten subjects with adult periodontitis and a group of four localized juvenile periodontitis. The supernatant was used as a specimen and its hydrolytic activity was determined according to the same manner as described in Experiment 4 except that the reaction was carried out at 37° C. for 4 hours. As the substrates, there were used N-carbobenzoxy-valyl-glycyl-arginine-p-nitrophenol (CxVGR-pNP), N-carbobenzoxy-valyl-glycylarginine-4-methoxy-2-naphthylamide (CxVGR-4NA) and N-carbobenzoxy-valyl-glycyl-arginine-$\beta$-naphthylamide (CxVGR-$\beta$NA). Color was developed by using 1N sodium hydroxide for CxVGR-pNP and Fast Blue BB for CxVGR-4NA and CxVGR-$\beta$NA. The results are shown in Table 7.

TABLE 7

| | Group (nmol/ml) | | |
|---|---|---|---|
| Substrate | Healthy subjects | Adult Periodontitis subjects | Localized juvenile periodontitis subjects |
| CxVGR-pNP | 17.0 ± 11.4 | 34.0 ± 9.7* | 32.5 ± 9.6** |
| CxVGR-4NA | 18.0 ± 10.8 | 34.6 ± 8.9* | 32.3 ± 8.9** |
| CxVGR-$\beta$NA | 16.1 ± 10.3 | 35.6 ± 9.8* | 33.4 ± 10.0** |

*$p < 0.01$
**$p < 0.05$

As shown in Table 7, both subjects with adult periodontitis and localized juvenile periodontitis have higher (activities) than healthy subjects and the difference is statistically significant.

EXPERIMENT 8

According to the same manner as described in Experiment 7, hydrolytic activity was tested by using lysyl-proline-p-nitroanilide (KP-pNA), lysyl-proline-4-methoxy-2-naphthylamide (KP-4NA) and lysyl-proline-$\beta$-naphthylamide (KP-$\beta$NA) as the substrates. Color was developed by using 1N sodium hydroxide for KP-pNA and Fast Blue BB for KP-4-NA and KP-$\beta$NA. The results are shown in Table 8.

TABLE 8

| | Group (nmol/ml) | | |
|---|---|---|---|
| Substrate | Healthy subjects | Adult Periodontitis subjects | Localized juvenile periodontitis subjects |
| KP-pNA | 15.0 ± 9.4 | 34.3 ± 9.8* | 31.5 ± 9.7** |
| KP-4NA | 16.0 ± 10.8 | 35.5 ± 10.1* | 32.3 ± 8.9** |
| KP-$\beta$NA | 16.1 ± 10.3 | 36.2 ± 9.9* | 33.4 ± 10.0** |

*$p < 0.01$
**$p < 0.05$

Likewise, both subjects with adult periodontitis and localized juvenile periodontitis have more than twice as high values (activities) as that of healthy subjects and the difference is statistically significant.

EXPERIMENT 9

According to the same manner as described in Experiment 7, hydrolytic activity was tested by using N-carbobenzoxy-valyl-glycyl-arginine-$\beta$-naphthylamide (CxVGR-$\beta$NA), N-benzoyl-arginyl-glycyl-phenylalanyl-proline-$\beta$-naphthylamide (BzRGFP-$\beta$NA), N-carbobenzoxy-valyl-glycylarginine-p-nitrophenol (CxVGR-pNP) and N-benzoyl-arginylglycyl-phenylalanyl-proline-p-nitrophenol (BzRGFP-pNP) alone or in combination as the substrates. The results are shown in Table 9.

TABLE 9

| | Group (nmol/ml) | | |
|---|---|---|---|
| Substrate | Healthy subjects | Adult Periodontitis subjects | Localized juvenile periodontitis subjects |
| CxVGR-$\beta$NA | 15.0 ± 8.8 | 34.8 ± 10.2* | 31.5 ± 9.8** |
| BzRGFP-$\beta$NA | 13.2 ± 5.4 | 27.8 ± 7.4* | 22.6 ± 5.3** |
| CxVGR-$\beta$NA + BzRGFP-$\beta$NA | 18.4 ± 8.3 | 50.2 ± 15.3* | 42.2 ± 13.4** |
| CxVGR-pNP | 14.0 ± 7.9 | 33.5 ± 11.5* | 28.8 ± 9.1** |
| BzRGFP-pNP | 13.3 ± 4.9 | 25.6 ± 8.4* | 21.8 ± 7.8** |
| CxVGR-pNP + BzRGFP-pNP | 18.6 ± 8.1 | 49.8 ± 14.4* | 44.5 ± 12.8** |

*$p < 0.01$
**$p < 0.05$

Likewise, both subjects with adult periodontitis and localized juvenile periodontitis have higher values (activities) than that of healthy subjects and the difference is statistically significant.

Accordingly, objective diagnosis and prognostication of periodontal diseases can be carried out by using the reagent of the present invention to determine hydrolytic activity of oral pathogenic microorganisms for periodontal diseases.

EXAMPLE 1

As a substrate solution, a solution of N-carbobenzoxy-valyl-glycyl-arginine-4-methoxy-2-naphthylamide in distilled water (2 mM) was prepared.

As a buffer, 0.1M Tris-HCl buffer (pH 7.0) was prepared.

As a coloring reagent, diazonium salt of Garnet GBC was dissolved in 1M acetate buffer (pH 4.0) containing 10% of Tween 20 at a concentration of 0.5 mg/ml.

These reagents were combined and used as a kit for testing for periodontal diseases.

This kit can be used for diagnosis of periodontal diseases as follows.

A paper point is inserted into the gingival crevice of a subject for 30 seconds to collect a specimen. The substrate solution (0.1 ml) and the buffer (0.9 ml) are mixed and the specimen is added to the mixture. The mixture is allowed to react at 37° C. for 24 hours. After completion of the reaction, the coloring reagent (0.3 ml) is added. After 15 minutes at room temperature, a color tone is observed by the naked eye. The intensity of brown color is evaluated by comparing with a blank control. Heavy brown color shows that the subject has periodontal diseases.

EXAMPLE 2

A substrate reagent was prepared by soaking a paper disc (diameter 0.6 cm) with N-benzoyl-valyl-glycyl-arginine-4-methoxy-2-naphthylamide (500 nmol).

0.1M Phosphate buffer (pH 7.2) was used as a buffer.

These reagents and the coloring reagent prepared in the same manner as described in Example 1 were combined and used as a kit for testing for periodontal diseases.

This kit can be used for diagnosis of periodontal diseases as follows:

The buffer solution (400 μl) was placed in a vial to which are added saliva (100 μl) collected from a subject and the paper disc of the substrate reagent. The mixture is reacted at 37° C. for 4 hours. After completion of the reaction, the coloring reagent is added and color development is evaluated by the naked eye according to the same manner as described in Example 1.

EXAMPLE 3

N-carbobenzoxy-arginyl-arginine-4-methoxy-2-naphthylamide (500 nmol) was lyophilized in an ampoule (inner diameter 5 mm; length 3 cm) to prepare a substrate reagent.

0.05M Tris-HCl buffer (pH 7.5) was prepared and used as a buffer.

Diazonium salt of Fast Blue B was dissolved in 1M acetate buffer (pH 4.2) containing 10% of Tween 20 at the concentration of 1 mg/ml and used as a coloring reagent.

These reagents were combined and used as the kit for testing for periodontal diseases.

This kit can be used for diagnosis of periodontal diseases as follows.

A paper strip is inserted into the gingival crevice of a subject for 30 seconds to collect a specimen. The buffer (1 ml) is poured in an ampoule containing the substrate to dissolve it. The specimen is added to the solution and reacted at 37° C. for 24 hours. After completion of the reaction, the coloring reagent (0.4 ml) is added and color development is evaluated according to the same manner as described in Example 1.

EXAMPLE 4

N-t-Butoxycarbonyl-leucyl-glycyl-arginine-β-naphthylamide was dissolved in 0.05M phosphate buffer (pH 7.2) in the concentration of 200 nmol/ml and a circular filter paper (diameter 1 cm) was soaked with the solution (100 μl), dried and placed at the bottom of a cuvette (inner diameter 1 cm) to prepare a substrate reagent.

This reagent was combined with the coloring reagent prepared in the same manner is described in Example 3 and used as a kit for testing for periodontal diseases.

This kit can be used for diagnosis of periodontal diseases as follows.

Saliva (100 μl) collected from a subject is added to the curvette and reacted at 37° C. for 4 hours. After completion of the reaction, the coloring reagent (40 μl) is added and color development is evaluated according to the same manner as described in Example 1.

EXAMPLE 5

According to the same manner as described in Example 1, a substrate solution was prepared except that lysyl-proline-4-methoxy-2-naphthylamide was used instead of N-carbobenzoxy-valyl-glycyl-arging-4-methoxy-2-naphthylamide.

The substrate solution can be used as a kit for testing for periodontal diseases according to the same manner as described in Example 1.

EXAMPLE 6

According to the same manner as described in Example 2, a substrate reagent was prepared except that lysyl-proline-4-methoxy-2-naphthylamide was used instead of N-benzoyl-valyl-glycyl-arginine-4-methoxy-2-naphthylamide.

This substrate reagent can be used as a kit for testing for periodontal diseases according to the same manner as described in Example 2.

EXAMPLE 7

According to the same manner as described in Example 3, a substrate reagent was prepared except that N-carbobenzoxy-prolyl-alanyl-glycyl-proline-β-naphthylamide was used instead of N-carbobenzoxy-arginyl-arginine-4- methoxy-2-naphthylamide.

This substrate reagent can be used as a kit for testing for periodontal diseases according to the same manner as described in Example 3.

EXAMPLE 8

According to the same manner as described in Example 4, a substrate reagent was prepared except that N-benzoyl-arginyl-glycyl-phenylalanyl-proline-β-naphthylamide instead of N-t-butoxycarbonyl-leucyl-glycyl-arginine-β-naphthylamide.

This substrate reagent can be used as a kit for testing for periodontal diseases according to the same manner as described in Example 4.

EXAMPLE 9

2 mM Solution of N-carbobenzoxy-valyl-glycyl-arginine-4-methoxy-2-naphthylamdie in distilled water was mixed with the same amount of 2 mM solution of N-benzoyllysyl-proline-4-methoxy-2-naphthyalamide in distilled water to prepare a substrate solution.

This substrate solution can be used as a kit for testing for periodontal diseases according to the same manner as described in Example 1.

EXAMPLE 10

A substrate reagent was prepared by soaking a paper disc (diameter 0.6 cm) with N-benxoyl-valyl-glycyl-arginine-4-methoxy-2-naphthylamide (500 nmol) and N-benzoyl-prolylalanyl-glycyl-proline-4-methoxy-2-naphthylamide (250 nmol).

This substrate reagent can be used as a kit for testing for periodontal diseases according to the same manner as described in Example 2.

EXAMPLE 11

N-carbobenzoxy-arginyl-arginine-4-methoxy-2-naphthylamide (500 nmol) and N-benxoyl-arginyl-glycyl-phenylalanyl-proline-β-naphthylamide (500 nmol) were lyophilized in an ampoule (inner diameter 5 mm; length 3 cm) to prepare a substrate reagent.

This substrate reagent can be used as a kit for testing for periodontal diseases according to the same manner as described in Example 3.

EXAMPLE 12

N-t-butoxycarbonyl-leucyl-glycyl-arginine-β-naphthylamide was dissolved in 0.05M phosphate buffer (pH 7.2) in a concentration of 400 nmol/ml. Likewise, lysylproline-β-naphthylamide was dissolved in 0.05M phosphate buffer (pH 7.2) in a concentration of 400 mnol/ml. The same amounts of both solutions were mixed and a circular filter paper (diameter 1 cm) was soaked with the mixture (100 μl), dried and placed at the bottom of a cuvette (inner diameter 1 cm) to prepare a substrate reagent.

This substrate reagent can be used as a kit for testing for periodontal diseases according to the same manner as described in Example 4.

What is claimed is:

1. A method for diagnosing contraction or progress of periodontal diseases which comprises determining periodontopathic bacteria specific aminopeptidase activity in a specimen by using as a substrate for the enzyme either or both compounds of the formula:

X-Z-Arg-Y     [1]

wherein Arg is arginine residue; X is an amino blocking group; Y is a color developing group attached to the C-terminal of Arg selected from the class consisting of β-naphthylamine, 4-methoxy-2-naphthylamine, p-nitrophenol, 7-amino-4-methoxycoumarine, dimethyl-5-aminoisophthalate and 7-amino-4-trifluoromethylcoumarin groups; and Z is an amino acid or peptide residue composed of 1 or 2 amino acids or their blocked derivatives, the C-terminal of which is attached to the N-terminal of Arg, and X'-Z'-Pro-Y'     [2]

wherein Pro is proline residue; X' is an amino blocking group Y' is a color developing group attached to the C-terminal of Pro; and Z' is an amino acid or peptide residue composed of 0 to 4 amino acids or their protected derivatives, the C-terminal of which is attached to the N-terminal of Pro.

2. A method according to claim 1, wherein X or X' is selected from the group consisting of formyl, acetyl, succinyl, t-butoxycarbonyl, benzoyl, carbobenzoxy and p-toluenesulfonyl.

3. A method according to claim 1, wherein Y' is a member selected from the class consisting of β-naphthylamine, 4-methoxy-2-naphthylamine, p-nitroaniline, p-nitrophenol, 7-amino-4-methoxycoumarin, dimethyl-5-aminoisophthalate and 7-amino-4-trifluoromethylcoumarin groups.

4. A method according to claim 1, wherein the C-terminal amino acid residue in Z is a residue of glycine, lysine, arginine, phenylalanine or a blocked derivative thereof.

5. A method according to claim 1, wherein the C-terminal amino acid residue in Z' is a residue of glycine, lysine, phenylalanine or a blocked derivative thereof.

6. A method according to claim 1, wherein the substrate is a compound of the formula [1].

7. A method according to claim 1, wherein the substrate is a compound of the formula [2].

8. A method according to claim 1, wherein the substrate is both compounds of the formulas [1] and [2].

* * * * *